United States Patent [19]
Becker

[11] 4,273,714
[45] Jun. 16, 1981

[54] TRICYCLIC LACTONES

[75] Inventor: Joseph J. Becker, Geneva, Switzerland

[73] Assignee: Firmenich, S.A., Geneva, Switzerland

[21] Appl. No.: 142,051

[22] Filed: Apr. 21, 1980

[30] Foreign Application Priority Data

Apr. 27, 1979 [CH] Switzerland ............... 3972/79

[51] Int. Cl.$^3$ ............................................. C07D 311/74
[52] U.S. Cl. ........................... 260/343.21; 252/522 R; 426/536; 131/277; 424/279
[58] Field of Search ..................................... 260/343.21

[56] References Cited

U.S. PATENT DOCUMENTS

| 3,981,892 | 9/1976 | Skorianetz | 260/343.21 |
| 4,159,258 | 6/1979 | Ohloff et al. | 260/343.21 |

OTHER PUBLICATIONS

Mueller et al., Chem. Abst. 27174W vol. 69 1968.

Primary Examiner—Henry R. Jiles
Assistant Examiner—Jane T. Fan
Attorney, Agent, or Firm—Scully, Scott, Murphy & Presser

[57] ABSTRACT

Novel tricyclic lactones, viz. 10,10-dimethyl-4-oxa-tricyclo[7.1.1.0$^{3,8}$]undec-3(8)-en-5-one and 10,10-dimethyl-4-oxa-tricyclo[7.1.1.0$^{3,8}$]undecan-5-one, and use thereof as perfuming or flavor-modifying ingredients.

3 Claims, No Drawings

TRICYCLIC LACTONES

BRIEF SUMMARY OF THE INVENTION

The instant invention relates to the field of perfumery and of the flavour industry, in particular it relates to novel tricyclic lactones having the formula

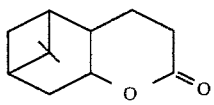
(I)

possessing a single or a double bond in the position indicated by the dotted line, as well as the use thereof as perfuming or flavour-modifying ingredients. The invention further relates to a perfume or flavour composition containing said lactones as active ingredients.

BACKGROUND OF THE INVENTION

In the perfumery as well as in the flavour industry a lot of efforts are devoted today to the replacement of expensive naturally occurring raw materials or the reproduction of original organoleptic effects by making use of new chemicals. Among the numerous synthetic odorants prepared in a recent past, bi-, tri- or polycyclic derivatives of decalin can be cited as examples, as well as bicyclo[2.2.1]heptane, bicyclo[2.2.2]octane, cedrene or caryophyllene derivatives.

For instance, the tricyclic compound of formula

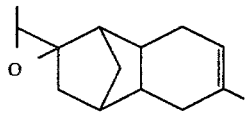

is appreciated in the art for its original floral and woody odour—see e.g. Swiss Pat. No. 547 850—, as well as the compound of formula

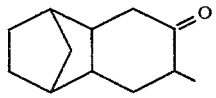

which is used in perfumery for developing or enhancing woody and spicy odour notes—see e.g. Swiss Pat. No. 557 870—. As further example of tricyclic fragrant compounds, one can also cite the compound of formula

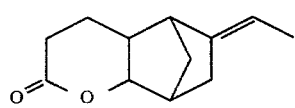

characterized by its original odour note, at the same time sweet, fresh, spicy and herbaceous—see e.g. DE-OS No. 28 26 302.

Notwithstanding the relative abundance of tricyclic fragrant compounds known in the art, there still remains a constant need of enrichment of the palette of the perfumer, or of the flavourist, by the finding of new active substances.

PREFERRED EMBODIMENTS OF THE INVENTION

I have surprisingly found that the tricyclic lactones of the invention, viz. 10,10-dimethyl-4-oxa-tricyclo[7.1.1.0$^{3,8}$]undec-3(8)-en-5-one and 10,10-dimethyl-4-oxa-tricyclo[7.1.1.0$^{3,8}$]undecan-5-one, are particularly useful ingredients for preparing both perfumes and flavour compositions.

In the field of perfumery, the compounds of formula (I) are characterized by their sweet, herb-like and slightly spicy note, reminiscent of that of tobacco, honey and tonka beans. The said compounds can thus be widely used in modern perfumery, for example as perfuming ingredients for the preparation of fruity, spicy, lactonic or "fougère" compositions to which they advantageously confer elegance and harmony. The compounds of formula (I) are also suitable for preparing perfumed articles such as soaps, detergents, household materials or cosmetic products, lotions, shampoos or beauty creams for example.

The proportions of compounds of formula (I) to be used for the achievement of the above cited olfactive effects may vary within a wide range and are more generally comprised between about 1 and 20 weight percent of the weight of the considered composition. Proportions higher or lower than those given above may also be used, depending on the particular effect which is desired. It must be added that 10,10-dimethyl-4-oxa-tricyclo[7.1.1.0$^{3,8}$]undec-3(8)-en-5-one is the preferred perfuming ingredient of the instant invention.

In the field of flavours, the compounds of formula (I) may be defined as possessing a taste and aroma of sweet, flowery, woody, herbal and coumarin type. They can thus advantageously be used for the preparation of various artificial flavours such as caramel, nut, coconut, honey or cocoa flavours, as well as flavours of the fruity type, cherry flavours e.g. The said compounds can also be used for flavouring foodstuffs, feedstuffs, beverages, pharmaceutical preparations or tobacco products.

The productions to be used for the achievement of the above mentioned gustative effects are generally comprised between about 1 and 100 ppm (parts per million) of the weight of the flavoured material. In the case of the aromatization of tobacco products, said proportions are more particularly comprised between about 100 and 200 ppm. However, higher or lower proportions than those given hereinabove can also be used, especially when more particular effects are desired. It must be added that 10,10-dimethyl-4-oxa-tricyclo[7.1.1.0$^{3,8}$]undec-3(8)-en-5-one is the preferred flavouring ingredient.

10,10-Dimethyl-4-oxa-tricyclo[7.1.1.0$^{3,8}$]undec-3(8)-en-5-one and 10,10-dimethyl-4-oxa-tricyclo[7.1.1.0$^{3,8}$]undecan-5-one, which are both novel compounds, can be easily prepared according to the usual techniques, by making use of pinocarvone as starting material as illustrated hereinbelow:

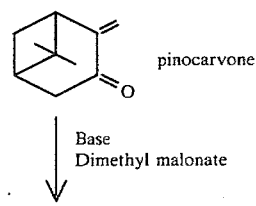
pinocarvone

Base
Dimethyl malonate

-continued

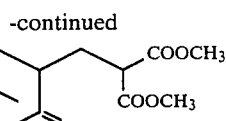

↓ Hydrolysis
  −CO₂

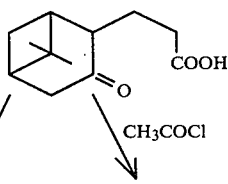

(1) Reduction
(2) Hydrolysis ↙     ↘ CH₃COCl

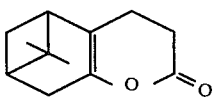

10,10-dimethyl-4-         10,10-dimethyl-4-oxa-
oxa-tricyclo              tricyclo[7.1.1.0³,⁸]
[7.1.1.0³,⁸]undecan-      undec-3(8)-en-5-one
5-one Pinocarvone, used hereinabove as starting material is a secondary product of the distillation of spanish eucalyptus oil—see S. Arctander, Perfume and Flavor Chemicals, Montclair N.J. 1969, Section 2624—. It can also be prepared from α-pinene, after epoxidation thereof, isomerization into pinocarveol and subsequent oxidation. The detail of the preparation of the compounds of the invention is described in the following examples (temperature in degrees centigrade).

EXAMPLE 1

10,10-Dimethyl-4-oxa-tricyclo[7.1.1.0³,⁸]undecan-5-one

To a mixture of 620 g (2.95 M) of 3-(6,6-dimethyl-3-oxo-bicyclo[3.1.1]hept-4-yl)-propionic acid, 150 g of sodium hydroxide and 5 l of water, there were added, in small portions and under nitrogen atmosphere, 45.6 g (1.20 M) of sodium borohydride in 350 g of 30% aqueous solution of sodium hydroxide. After stirring of the reaction mixture at room temperature for 3 hours and 4 further hours at 35°, there were added thereto 1520 ml of $H_2SO_4$ 25% in water. After heating of the acidic reaction mixture at 80° during 15 minutes, then addition of 1 l of toluene at about 50°, the whole mixture was kept overnight at room temperature. After washing of the organic layer with water (2×1000 ml) and evaporation of the volatile parts under reduced pressure (15 Torr) there were obtained 650 g of crude material.

The above crude material was then distilled twice, to afford 425 g (74% yield) of the desired compound having b.p. 120°-125°/0.06 Torr.

IR: 2900, 1730 cm⁻¹

NMR: signals at 0.95, 1.28, 1.62-2.30, 2.75, 4.38 δ ppm

MS: M⁺=194(2); m/e=179(5), 153(5), 134(9), 125(60), 107(12), 97(23), 82(100), 67(37), 55(54), 41(54), 27(18).

3-(6,6-Dimethyl-3-oxo-bicyclo[3.1.1]hept-4-yl)-propionic acid used hereinabove as starting material was prepared as follows:

(a) 300 g (2.0 M) of pinocarvone were added to a mixture of 400 g (3.0 M) of dimethyl malonate, 100 ml of methyl alcohol and 30 g of sodium methoxide maintained at 30°. During the addition, the temperature reached 65° and was finally kept at 78° for 1 hour. After cooling to room temperature, addition of 300 ml of toluene, then 60 ml of acetic acid and finally 200 ml of water, the organic layer was washed with water (300 ml), dried over $Na_2SO_4$ and evaporated under reduced pressure (15 Torr) to afford 700 g of crude material.

After distillation thereof, there were isolated 500 g (98% yield) of the desired addition product having b.p. 140°-150°/0.1 Torr.

(b) 560 g (1.98 M) of the above addition product were added to a mixture of 250 ml of acetic acid, 100 ml of water and 35 g of benzenesulfonic acid placed in a reactor fitted with a distillation device. The reaction mixture was then heated to 80°-95° and the formed methyl acetate was distilled over a period of about 8 hours (b.p. 52°-55°).

After a first distillation on a VIGREUX column (pressure: 15 Torr—elimination of the excess of acetic acid), the remaining residue was diluted with 200 ml of ethyl acetate, washed with an aqueous solution of NaCl (200 ml), then with an aqueous solution of NaCl and sodium acetate (170 ml). After drying over $Na_2SO_4$ and evaporation, there were obtained 450 g of crude residue.

After final distillation, there were isolated 335 g of 3-(6,6-dimethyl-3-oxo-bicyclo[3.1.1]hept-4-yl)-propionic acid having b.p. 140°-160°/0.5 Torr; m.p. 45°.

IR: 3300-2800, 1700 cm⁻¹

NMR: signals at 0.90, 1.30, 1.34, 2.10, 2.3, 2.7, 11.2 δ ppm.

EXAMPLE 2

10,10-Dimethyl-4-oxa-tricyclo[7.1.1.0³,⁸]undec-3(8)-en-5-one 80 ml of acetyl chloride were added dropwise to a hot (60°) mixture of 84 g (0.4 M) of 3-(6,6-dimethyl-3-oxa-bicyclo[3.1.1]hept-4-yl)propionic acid—see Example 1—and 400 ml of carbon tetrachloride. After heating to reflux for 4 hours, the reaction mixture was kept overnight at room temperature, then successively washed with water and sodium acetate 10% in water, dried over $Na_2SO_4$ and finally evaporated to afford 80 g of crude material.

After distillation, there were isolated 65 g (85% yield) of the desired compound having b.p. 90°-100°/0.12 Torr; m.p. 60° (recrystallized in ethyl alcohol).

IR: 3500, 2900, 1740 cm⁻¹

NMR: signals at 0.86, 1.30, 1.88-2.36 δ ppm

MS: M⁺=192(15); m/e=177(2), 149(73), 135(10). 121(8), 107(16), 91(12), 81(66), 67(14), 55(100), 41(42), 27(15).

EXAMPLE 3

A base perfume composition for a masculine "Eau de toilette" was prepared as indicated hereinafter.

| Ingredients | Parts by weight |
| --- | --- |
| Bergamot oil | 240 |
| VETYRISIA ®¹ | 200 |
| Lavender oil 48/50 | 60 |
| Lemon oil (terpenless) | 50 |
| Treated birch tar oil 10%* | 50 |
| Galbanum oil 10%* | 50 |
| Hydroxycitronellal² | 30 |
| Rosemary oil | 30 |

-continued

| Ingredients | Parts by weight |
| --- | --- |
| Neroli bigarade oil | 20 |
| Geranium Bourbon oil | 20 |
| Incense resinoid 50%* | 20 |
| Oak moss absolute (discolourized) 50%* | 20 |
| Levo-citronellol | 20 |
| FIXATEUR 404[3] 10%* | 20 |
| Nutmeg oil | 15 |
| Cubeba oil | 5 |
| Total | 850 |

*in diethyl phthalate
[1]origin : FIRMENICH SA
[2]CYCLOSIA ® (FIRMENICH SA)
[3]Origin : FIRMENICH SA (see S. Arctander, Perfume and Flavor Chemicals, Montclair NJ 1969, Section 1391)

The above base composition, which is characterized by a pleasant leathery, spicy and woody odour, is particularly suitable for preparing masculine cosmetic preparations such as "Eau de toilette" or aftershave lotions e.g.

By adding 15 parts of 10,10-dimethyl-4-oxa-tricyclo[7.1.1.0$^{3,8}$]undec-3(8)-en-5-one to 85 parts of the above base, there was obtained a new perfume composition having a dominating spicy note, the overall odour of which was qualified as more elegant and more harmonious than that of the said base.

An analogous, but less marked, olfactive effect was observed when, in the above example, 10,10-dimethyl-4-oxa-tricyclo[7.1.1.0$^{3,8}$]undec-3(8)-en-5-one was replaced by 10,10-dimethyl4-oxa-tricyclo[7.1.1.0$^{3,8}$]undecan-5-one.

EXAMPLE 4

The two following beverages were flavoured with 10,10-dimethyl-4-oxa-tricyclo[7.1.1.0$^{3,8}$]undec-3(8)-en-5-one as indicated hereinafter (dosage):

(a) commercial pasteurized milk (2.5 ppm)
(b) commercial cherry juice (3.0 ppm).

The thus flavoured (test) samples were then subjected to organoleptic evaluation by comparison with an unflavoured (control) material. The results of the said evaluation are summarized as follows:

(a) enhanced sweet note, slightly caramel-like
(b) more intense sweet and fruity taste, slightly flowery.

An analogous, but less marked, olfactive effect was observed when, in the above example, 10,10-dimethyl-4-oxa-tricyclo[7.1.1.0$^{3,8}$]undec-3(8)-en-5-one was replaced by 10,10-dimethyl-4-oxa-tricyclo[7.1.1.0$^{3,-}$$^{8}$]undecan-5-one.

EXAMPLE 5

1.5 g of a 1% solution of 10,10-dimethyl-4-oxa-tricyclo[7.1.1.0$^{3,8}$]undec-3(8)-en-5-one in 95% ethyl alcohol were sprayed onto 100 g of a mixture of tobacco of "american blend" type. The tobacco thus flavoured was used to manufacture test cigarettes which were then subjected to organoleptic evaluation by comparison with non-flavoured cigarettes (control). The tobacco used to manufacture the control cigarettes was preliminary treated with 95% ethyl alcohol.

The results of such an evaluation are summarized hereinafter:

1. odour of tobacco before smoking: herbal and flowery note, typical tobacco odour more intense than that of the control sample.
2. taste and aroma of cigarettes smoke: sweet, herbal and flowery effect of coumarin type, more pronounced than that of the control sample.

An analogous, but less marked, olfactive effect was observed when, in the above example, 10,10-dimethyl-4-oxa-tricyclo[7.1.1.0$^{3,8}$]undec-3(8)-en-5-one was replaced by 10,10-dimethyl-4-oxa-tricyclo[7.1.1.0$^{3,-}$$^{8}$]undecan-5-one.

What I claim is:

1. A compound of the formula

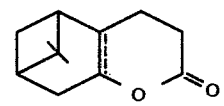

(I)

possessing a single or a double bond in the position indicated by the dotted line.

2. 10,10-Dimethyl-4-oxa-tricyclo[7.1.1.0$^{3,8}$]undec-3(8)-en-5-one.

3. 10,10-Dimethyl-4-oxa-tricyclo[7.1.1.0$^{3,8}$]undecan-5-one.

* * * * *